(12) United States Patent
Rotramel

(10) Patent No.: US 6,171,314 B1
(45) Date of Patent: Jan. 9, 2001

(54) METHOD AND APPARATUS FOR MAINTAINING OPEN AIR PASSAGEWAYS

(76) Inventor: Stuart L. Rotramel, 1204 Briarcliff, Mahomet, IL (US) 61853

( * ) Notice: Under 35 U.S.C. 154(b), the term of this patent shall be extended for 0 days.

(21) Appl. No.: 09/176,858

(22) Filed: Oct. 22, 1998

Related U.S. Application Data

(60) Provisional application No. 60/065,715, filed on Nov. 14, 1997.

(51) Int. Cl.$^7$ ..................................................... A61D 1/12
(52) U.S. Cl. ............................................. 606/106; 602/18
(58) Field of Search .............................. 606/106; 602/18, 602/17, 19, 32; 128/DIG. 23, 68, 87, 76, 200.24, 207.18, 845, 876, 846

(56) References Cited

U.S. PATENT DOCUMENTS

| | | |
|---|---|---|
| 2,658,506 | 11/1953 | Haskell . |
| 2,668,577 | 2/1954 | Vanderschel . |
| 2,831,482 | 4/1958 | Cobb . |
| 2,904,040 * | 9/1959 | Hale ........................ 128/87 |
| 2,940,442 | 6/1960 | Wilhelm . |
| 2,954,026 | 9/1960 | Spinks . |
| 3,029,447 | 4/1962 | Maertins . |
| 3,077,613 | 2/1963 | Mayer . |
| 3,132,647 | 5/1964 | Corniello . |
| 3,276,444 | 10/1966 | Rice . |
| 3,286,283 | 11/1966 | Bertoldo . |
| 3,596,655 | 8/1971 | Corcoran . |
| 3,710,783 | 1/1973 | Jascalevich . |
| 4,454,870 | 6/1984 | Schwentker . |
| 4,538,598 | 9/1985 | Gill et al. . |
| 4,608,969 | 9/1986 | Hamlin . |
| 4,624,245 | 11/1986 | Mullin et al. . |
| 4,676,240 | 6/1987 | Gardy . |
| 4,700,697 * | 10/1987 | Mundell et al. ........................ 128/75 |
| 4,782,824 * | 11/1988 | Davies ................................... 128/68 |
| 5,129,881 | 7/1992 | Pope . |
| 5,147,287 | 9/1992 | Jewell et al. . |
| 5,499,633 | 3/1996 | Fenton . |
| 5,624,439 | 4/1997 | Edwards et al. . |
| 5,632,283 | 5/1997 | Carden . |
| 5,640,974 | 6/1997 | Miller . |
| 5,669,377 | 9/1997 | Fenn . |
| 5,690,121 | 11/1997 | Miller . |

* cited by examiner

Primary Examiner—Michael Buiz
Assistant Examiner—Lien Ngo
(74) Attorney, Agent, or Firm—Cook, Alex, McFarron, Manzo, Cummings & Mehler, Ltd.

(57) ABSTRACT

Apparatus and method for maintaining open air passageways in a human are disclosed. The apparatus includes at least one central support member and may include side support members. The support members include a chin contacting surface and body contacting surfaces. Placement of the apparatus under the chin of the human in a supine position maintains air passageways of the human substantially open. The apparatus and method are particularly useful in maintaining open air passageways in humans undergoing surgical procedures requiring anesthesia.

12 Claims, 3 Drawing Sheets

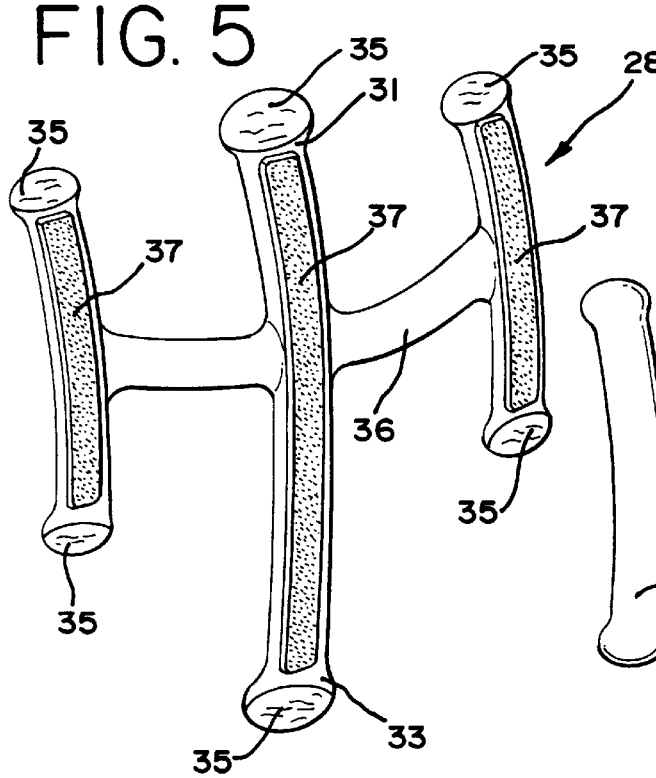
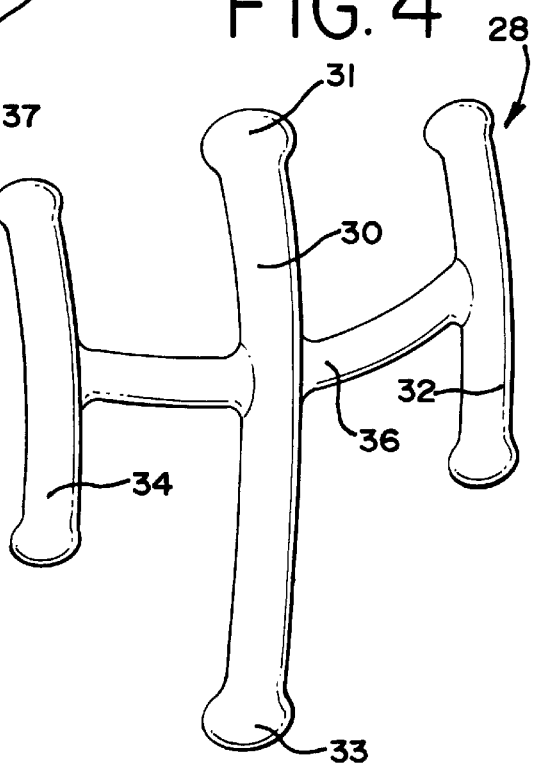
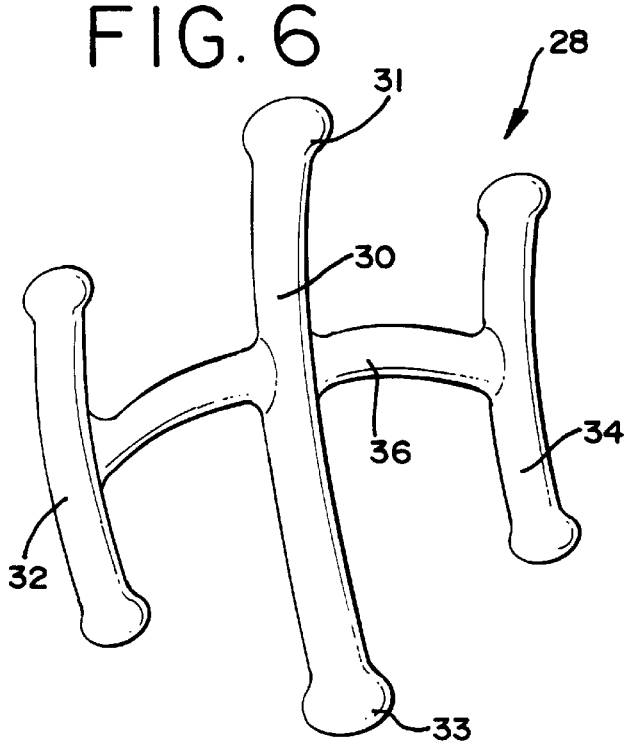
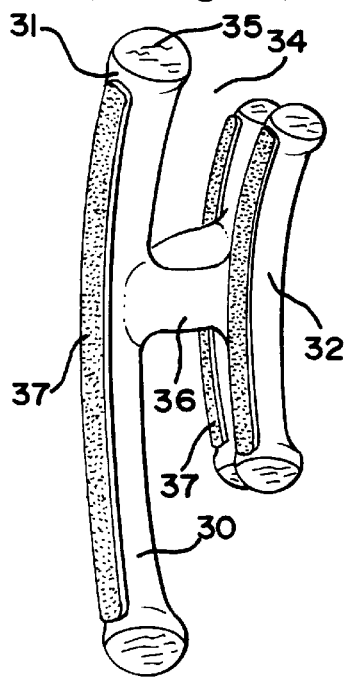

METHOD AND APPARATUS FOR MAINTAINING OPEN AIR PASSAGEWAYS

CROSS-REFERENCE TO RELATED APPLICATIONS

This application claims the benefit of provisional patent application Serial No. 60/065,715 filed on Nov. 14, 1997.

BACKGROUND

Oxygen is essential to human life. Without oxygen, human cells cannot carry out their basic metabolic functions and will eventually die. As the cells die, the human organs and tissues (which are made up of cells) eventually cease to function. For example, depriving human brain cells of oxygen for as little as five minutes can cause brain damage or even death.

The process by which humans (as well as other animals) take in and utilize oxygen is commonly referred to as "respiration." In the case of humans, respiration generally involves the continuous intake of oxygen from the air (which oxygen is then used by the cells) and release of by-products such as carbon dioxide to the outside environment. Inhalation or breathing allows the oxygen to enter the body and travel to the lungs, where it permeates the membranes of the lungs and eventually passes into the blood. The oxygen-laden blood then carries the oxygen throughout the body and, more particularly, to the cells that require it in order to sustain the living tissues and organs of the human body. As it reaches the cells, the blood exchanges its oxygen for the by-products of cellular metabolism, such as carbon dioxide. As it returns to the region of the lungs, the blood transports the carbon dioxide released by the cells. The carbon dioxide leaves the blood, enters the lungs and is released to the outside environment by exhalation. Upon release of carbon dioxide, the blood absorbs additional oxygen and the cycle is repeated.

The respiratory system facilitates the above-described exchange of oxygen for carbon dioxide. The human respiratory system is made up of a network of passageways that allows oxygen to enter the body and eventually make its way to the lungs. For example, during inhalation, oxygen is drawn in through the nostrils of the nose, from where it enters the nasal cavity. From the nasal cavity it travels through a region known as the pharynx which is located generally near the jaw region of the human. From the pharynx, the oxygen travels to the trachea, a passageway near the throat, and ultimately enters the lungs where the above-described cycle of oxygen absorption and carbon dioxide release takes place.

In humans, the nasal passageway is separated from the oral passageway (i.e. the mouth and mouth cavity) by a skeletal/muscular structure called the palate. The palate is made up of an anterior (front) bony hard palate and posterior (rear) soft palate. The nasal and oral passageways remain separated from each other except, for example, near the region of pharynx where the oral passageway intersects the nasal passageway. Thus, blockage of the nasal passageway upstream of the intersecting point would still allow for the intake of oxygen by breathing through the mouth and, thus, maintaining satisfactory respiratory function. However, obstruction of the pharynx at or near the point of intersection prevents oxygen inhaled through either the nose or the mouth from reaching the lungs.

Such obstruction near the pharynx often occurs at rest or during sleep, when the muscles of the human are in a relaxed state. For example, during relaxation, such as during sleep, the muscles of the neck and jaw relax causing the tongue to fall toward the soft palate. Also, as the muscles of the jaw relax, the chin falls toward the chest, causing the soft tissue of the soft palate to contact and close off the posterior pharynx, thereby causing a mild to moderate airway obstruction.

Typically, in an effort to overcome this obstruction, the diaphragm contracts and the chest muscles expand the chest with much strength, in an attempt to cause inspiration. These muscles then relax, usually after one to three seconds of effort, whether or not any air was exchanged into the lungs. This gives the appearance of breathing even though no air is moving into and out of the lungs. This may sometimes be described as a "false breath" or "obstructed breath". Typically as a person's oxygen levels fall, the urge to breathe becomes progressively stronger until air is exchanged (or the person expires). The strong inspiratory effort described above causes the relaxed structures (e.g. soft palate) described above to flap noisily when the inspiratory effort overcomes the obstruction. This is commonly known as a snore.

After several false breaths (sometimes referred to as sleep apnea), the arterial oxygen levels in the person fall to levels which cause the person to consciously or unconsciously open their airway in order to get air. This is an extremely strong drive which is basic to life. A person will awaken to a sufficient level to which breathing is possible. In some persons a small movement of the head or neck will open the airway. Others need to awaken almost completely in order to allow the increased muscle tone and/or head or neck movement to open the airway. Often at this point, the person may appear confused or startled, and may move about in order to get air into their lungs and thereby stay alive.

Keeping the airways open is of particular concern during surgical procedures where an anesthetic has been administered (typically by an anesthesiologist or an anesthetist) to cause muscle relaxation and sleep in the human patient. Administration of a general anesthetic causes the muscles of the body to relax, which often results in constriction of the posterior pharynx and closing of the airway in the manner described above.

During surgeries that utilize general anesthesia the respiratory drive is often sufficiently reduced to the point that a patient may show a greatly decreased response to hypoxia (or lowered blood oxygen levels). If the airways are allowed to become (and remain) obstructed, the patient may quietly expire.

One way of keeping the air flow moving is to insert an endotracheal tube (ETT) via the patient's mouth, thereby allowing air to enter the lungs through the mouth. This procedure is often referred to as "intubating." Unfortunately, intubating using an ETT or other similar device is not without its drawbacks. For example, removal of the ETT can sometimes cause irritation of the throat and, more specifically, of the vocal chords. Such irritation can result in spasm of the vocal chords (sometimes referred to as laryngeal spasm), which may require emergency treatment by the anesthesiologist.

Where an ETT is not used, ensuring that the air passageways remain open and unobstructed is done manually by the physician-anesthesiologist or the nurse-anesthetist. Keeping the air passageway open often requires the anesthesia provider to tilt and hold the chin of the patient in a backward fashion to avoid having the soft palate constrict the posterior pharynx as described above. During long surgical procedures, the continuous holding of the chin can become quite tedious and uncomfortable for the anesthesia provider.

Another concern during surgeries is the sudden reaction of a patient to air obstruction. Obstruction of the posterior pharynx may, in some patients (particularly those with thick necks, large tongues or those that are obese), occasionally cause such patients to suddenly awake or move as they attempt to open the blocked airway. Such sudden movements are at the very least, distracting to the surgeon performing the procedure and, in cases where the surgery is particularly delicate, such as in cataract surgery, may be quite dangerous.

Thus, it would be desirable to provide an apparatus that will keep the air passageways of a patient open and, at the same time, relieve the anesthesia provider from the strain of having to hold the patient's chin. Beyond surgical procedures, it is also desirable to provide an apparatus that will reduce or eliminate snoring and possibly sleep apnea.

BRIEF DESCRIPTION OF THE DRAWINGS

FIG. 4 is a perspective view of an apparatus embodying the present invention.

FIG. 5 is a perspective view of an apparatus embodying the present invention with Velcros strips and padded contacting surfaces.

FIG. 6 is a rear view of an apparatus embodying the present invention.

FIG. 7 is a side view of an apparatus embodying the present invention.

SUMMARY OF INVENTION

The present invention is generally directed to an apparatus for maintaining open air passageways. The apparatus includes at least one support member having a first end and a second end. The first end of the support member includes a chin contacting surface and the second end of the support member includes a body contacting surface.

In accordance with another aspect of the present invention, the apparatus also includes at least one side support member having a first end and a second end. The first end of the side support member may include a jaw contacting surface and the second end of the side support member may include a body contacting surface.

In another aspect of the present invention, the apparatus may include two side support members having first ends and second ends as generally described above.

In accordance with another aspect of the present invention, the central support member and one or more side members may be joined to a horizontal member.

In accordance with another aspect of the present invention, the apparatus may be made of any material such as plastic, rubber, foam and/or wood.

In accordance with another aspect of the present invention, the central and/or side support members may be curved and the chin contacting and chest contacting surfaces may be padded.

The present invention is also directed to a method of opening the airways of a human subject. The method includes placing the human subject in a supine position and positioning a support member between the chin and chest of the human subject.

DETAILED DESCRIPTION OF THE DRAWINGS

Figure 1:
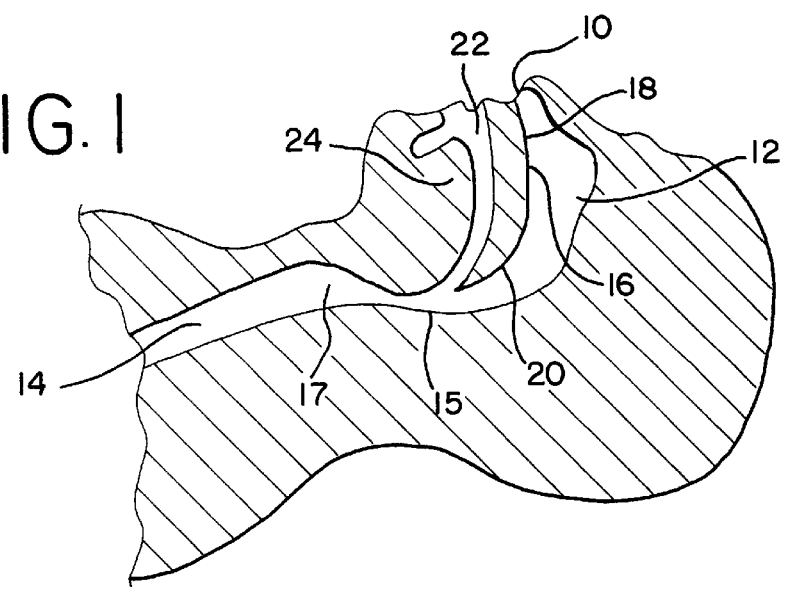
FIG. 1 is a side view of a portion of the human respiratory system with the nasal airway and oral passageway generally open.
Figure 2:
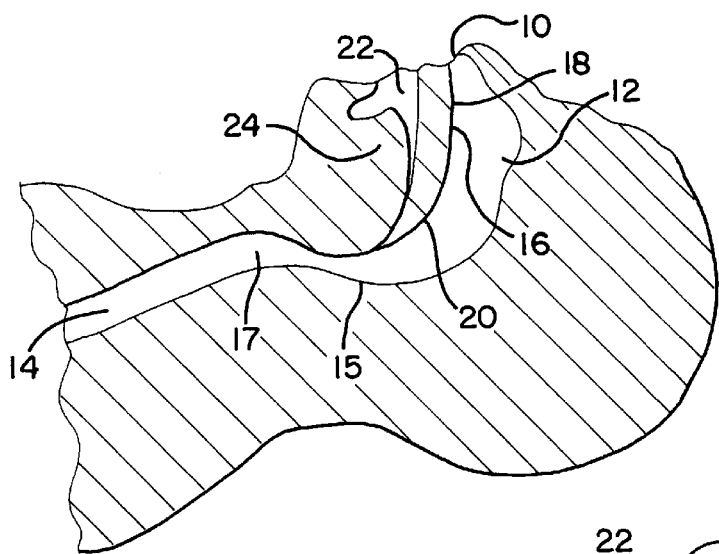
FIG. 2 is a side view of a portion of the human respiratory system with the nasal airway generally open.
Figure 3:
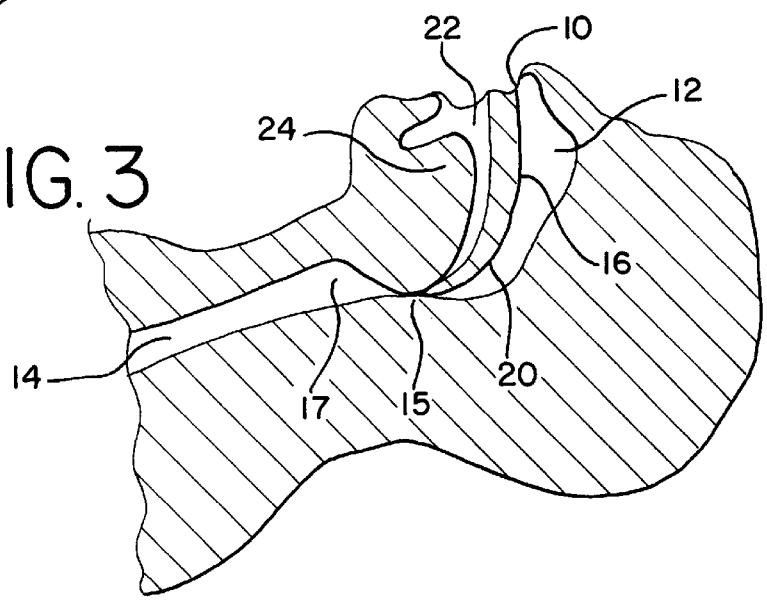
FIG. 3 is a side view of a portion of the human respiratory system with the nasal airway and oral passageway generally closed.

Turning now to the drawings, FIGS. 1, 2 and 3 show the upper portion of the human respiratory system. In the human respiratory system, oxygen enters the body through nostrils 10 and travels through nasal passageway 12 to the trachea 14 and ultimately to the lungs (not shown). As it travels from the nasal passageway 12 to the trachea 14, oxygen passes through the pharynx area 15. The area just below the pharynx area 15 and above the trachea is known as the larynx 17, commonly referred to as the "voice-box." Below nasal passageway 12 is the palate 16 which separates the nasal passageway 12 from the oral cavity 22 and tongue 24. The palate 16 includes an anterior (front) hard palate 18 and a posterior (rear) soft palate 20.

In a patient who is awake, the nasal passageway 12 remains substantially open as shown in FIG. 1 (where both the nasal passageway 12 and oral passageway 22 are open) and FIG. 2 (where the nasal passageway 12 is open, but the subject's mouth and, therefore, oral cavity are closed). However, during rest or sleep, when the muscles of the neck and jaw relax, palate 16, as shown in FIG. 3, constricts the oral and nasal passageways near the pharynx area 15, thereby obstructing the flow of air to the lungs.

Turning now to FIG. 4, there is shown one embodiment of the chin support 28 of the present invention. As shown in FIG. 4, chin support 28 includes a central support member 30. One end of central support member 30 includes a chin contacting surface 31 and the opposite end of the support member includes a chest contacting surface 33. Chin support 28 may also include at least one side support member. For example, as shown in FIG. 4, chin support 28 includes two side support members 32 and 34. Central support member 30 and side supports 32 and 34 may be integral with or connected together by horizontal member 36.

Chin support 28 may be made of any material that is suitable for supporting the chin in a substantially upright position. For example, chin support 28 may be made of a plastic such as a sturdy polymeric material that is, preferably, sterilizable. Suitable materials may include polymers (or copolymers) such as, for example, polyvinyl chloride, polyethylene, or elastomers, such as natural or synthetic rubber. Depending on the degree of support required, chin support 28 may also be made of other less rigid materials such as foam (which may include polystyrene or polyurethane). In the case of rubber, chin support may be made of a solid rubber or an inflatable rubber. In another alternative, chin support may be made of wood. If chin support 28 is made of a more flexible material (such as foam or rubber) and greater support is required (for example, for larger patients), the chin support may include an internal stiffener, such as but not limited to wood. Chin support 28 may be made by molding, such as, where appropriate, injection molding or compression molding. Other processes which would be apparent to one of skill in the art may also be used to make or form chin support 28 without departing from the present invention.

Chin support 28 may be made of a single integral piece or may be made up of several separate pieces (e.g. central 30 and side 32, 34 supports horizontal member 36) which can be assembled just prior to the time of use. In one embodiment, chin support 28 may be of a fixed size or, in another embodiment, may include support members of variable length. For example, depending on the size of the patient, central support member 30, side support members 32 and 34 or horizontal member 36 may be extendable to accommodate patients of different sizes or to provide additional comfort or control for the physician.

Figure 10:
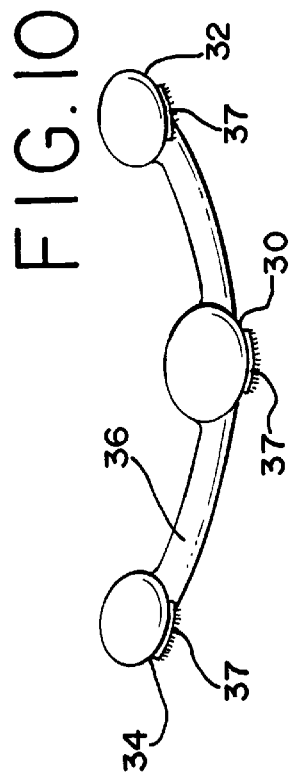
FIG. 10 is a top view of an apparatus embodying the present invention.
Figure 11:
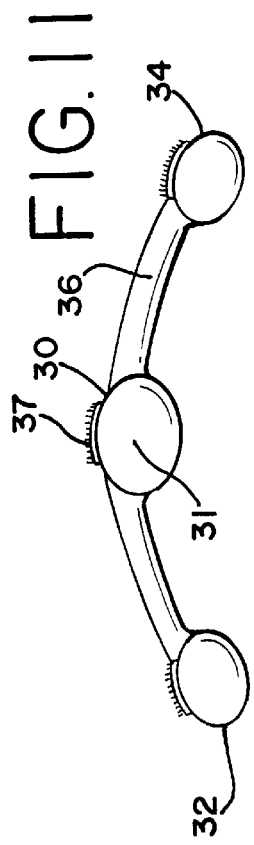
FIG. 11 is a bottom view of an apparatus embodying the present invention.

As shown in FIG. 4 and more clearly in FIG. 7, the surface of central support member 30 may be slightly curved or convex from top to bottom. The surface of horizonal member 36 may also be a curved or convex as it extends from side support 32 to side support 34 as shown in FIGS. 10 and 11. Chin support 28 may further include foam or otherwise padded ends 35 at the top and bottom ends of central support member 30 and side support members 32 and 34, as shown, for example, in FIGS. 5 and 7 to provide greater comfort to the patient, particularly at those points where chin support 28 is in contact with the patient. In addition, as shown in FIGS. 4–7, the ends of the support members 32 and 34 may be contoured so as to provide as much surface area for supporting the chin, jaws and/or for contacting the chest. Chin support 28 may also include Velcro® strips 37 on the front surfaces of central and side support members as shown, for example, in FIGS. 5 and 7. The Velcro® strips may be used to secure chin support 28 to the human subject as discussed in more detail below.

Figure 9:
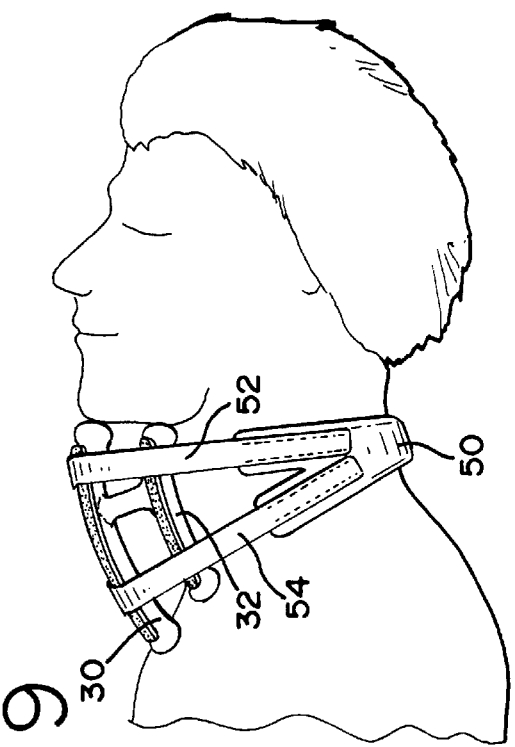
FIG. 9 is a side view of an apparatus embodying the present invention in use with a human subject.
Figure 8:
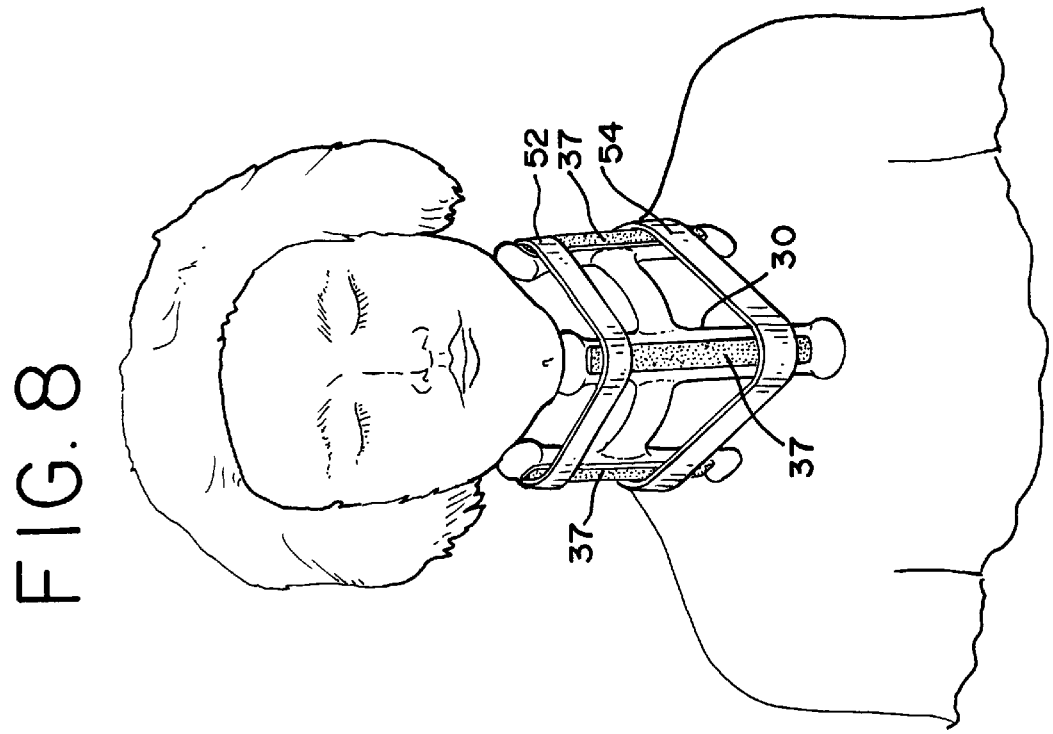
FIG. 8 is a front perspective view of an apparatus embodying the present invention in use with a human subject.

In accordance with the method of opening the airways of a human subject and/or maintaining opening airways using the above described chin support 28, as shown in FIGS. 8–9, the patient is typically placed in a supine position. Chin support 28 is positioned such that one end of central support member 30 is placed against the chin of the human subject and the opposite end of central support member 30 is allowed to rest on the body, and more particularly, the chest of the human subject. Similarly, the ends of side supports 32 and 34 are placed against the jaw of the human subject and the opposite ends of the side supports 32 and 34 are allowed to rest on the body (for example, the chest or clavicle) of the human patient. As set forth above, the support members 30, 32 and 34 may be adjustable and/or extendable to further push the chin of the human subject away from the chest if desired.

As shown in FIGS. 8 and 9 chin support may be secured to the human subject by collar 50. In one embodiment, as shown, for example, in FIGS. 8 and 9, the chin support 28 includes one or more straps 52 and 54 which are placed transversely over central and side supports 30, 32 and 34. The ends of straps 52 and 54 may be secured to each other behind the neck of the patient as generally shown in FIG. 9. Straps 52 and 54 may be permanently attached to chin support 28 or, in the alternative, removable. For example, as shown in FIGS. 5 and 7, support members 30, 32 and 34 may include Velcro® strips 37 to allow the straps 52 and 54 to physically engage chin support 28, thereby providing further stability and decreasing the chance that chin support 28 will slip from its desired position. Of course, it will be understood that chin support 28 may be secured in place by other means and without the use of Velcro® (such as, but not limited to, by a belt or strap alone).

Placement and use of chin support 28 in the manner described above "lifts" the chin and keeps it from dropping toward the chest, which in turn prevents the soft palate and/or tongue from blocking the area of the posterior pharynx. As a result, the passage of air through the nasal passageway to the lungs remains substantially uninhibited, without the need for constant manual manipulation by the anesthesia provider. By providing improved oxygenation, chin support 28 also decreases the build up of carbon dioxide in the patient (which can often lead to increased confusion in the patient undergoing sedation). Moreover, chin support 28 decreases restlessness and "startle" responses in sedated patients by helping maintain open airways. Chin support 28 may also improve surgical outcomes by improving the oxygenation of body tissues and, in general, makes airway management easier. Finally, chin support 28 may also be used for reducing or eliminating snoring. Of course, there may be other advantages of chin support 28 that may be recognized by those of skill in the art.

What is claimed is:

1. Chin-supporting apparatus comprising:
    a central support member having a chin-contacting end, a chest contacting end and a middle portion therebetween;
    a first side support member located to one side of and spaced from said central support member, said first side support member having a jaw-contacting end and a body contacting end;
    a second side support member located to the other side of and spaced from said central support member, said second side support member having a jaw-contacting end and a body contacting end; and
    a horizontal member directly connecting said side support members with said central support member at said middle portion.

2. The chin-supporting apparatus of claim 1 wherein said support member ends comprise a contoured surface area.

3. The chin-supporting apparatus of claim 1 where said apparatus is made from a material selected from the group consisting of plastic, rubber, foam and wood.

4. The apparatus of claim 1 further comprising an internal stiffener.

5. The apparatus of claim 1 wherein said central support member, said side support members, and said horizontal member are integral.

6. The apparatus of claim 1 wherein said central support member has a length greater than said side support members.

7. The apparatus of claim 1 wherein at least said central support member is curved and generally convex.

8. The apparatus of claim 1 wherein at least said chin and jaw contacting ends are padded.

9. The apparatus of claim 1 wherein the length of at least one of said support members is adjustable.

10. The apparatus of claim 1 further comprising a collar.

11. The apparatus of claim 1 wherein said collar is transversely affixed to at least said central support member.

12. The apparatus of claim 1 comprising means for attaching said collar to said central support member.

* * * * *